(12) United States Patent
Hoffman et al.

(10) Patent No.: US 6,329,158 B1
(45) Date of Patent: *Dec. 11, 2001

(54) USE OF DIMLY FLUORESCING NUCLEIC ACID DYES IN THE IDENTIFICATION OF NUCLEATED CELLS

(75) Inventors: Robert A. Hoffman, Livermore; Thomas Frey, San Jose, both of CA (US)

(73) Assignee: Becton Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/528,828

(22) Filed: Sep. 15, 1995

(51) Int. Cl.[7] .................. G01N 33/533; G01N 33/53; G01N 21/76; C12Q 1/68
(52) U.S. Cl. .................. 435/7.24; 435/6; 436/546; 436/547; 436/548; 436/172
(58) Field of Search .................. 435/6, 7.24, 7.92–7.95, 435/968; 436/546, 547, 548, 800, 805, 172; 424/534

(56) References Cited

U.S. PATENT DOCUMENTS

| | | | |
|---|---|---|---|
| 4,727,020 | * | 2/1988 | Recktenwald . |
| 4,957,870 | * | 9/1990 | Lee et al. . |
| 5,047,321 | * | 9/1991 | Loken et al. . |
| 5,057,413 | * | 10/1991 | Terstappen et al. . |
| 5,436,134 | * | 7/1995 | Haugland et al. . |
| 5,437,980 | * | 8/1995 | Haugland . |

OTHER PUBLICATIONS

Streitwieser and Heathcock "Introduction to Organic Chemistry, second edition" Macmillan Publishing Co, Inc (1981) p. 1156.*

Davis et al. "Clinical Flow Cytometric Reticulocyte Analysis", Pathobiology 1990; 58:99–106.*

Lee et al Biosis Abstract Accession No. 87:62136, 1986.*

* cited by examiner

*Primary Examiner*—Gary L. Kunz
*Assistant Examiner*—Stephen Gucker
(74) *Attorney, Agent, or Firm*—David M. Schneck

(57) ABSTRACT

This invention presents improved methodology for identification of nucleated cells in flow cytometric analysis when immunofluorescent dyes are also used. Briefly, in the method nucleic acids are stained with a fluorescent dye which can then be used to identify the nucleated cells by measurement of fluorescence on a flow cytometer. The improvement presented by this invention is the use of a saturating (or near saturating) amount of a nucleic acid dye, or mixture of dyes, which gives low fluorescence at excitation conditions, so as not to greatly interfere with the signals of the immunofluorescent dyes.

13 Claims, 4 Drawing Sheets

USE OF DIMLY FLUORESCING NUCLEIC ACID DYES IN THE IDENTIFICATION OF NUCLEATED CELLS

BACKGROUND OF THE INVENTION

The identification of nucleated cells in multi-parameter flow cytometric analysis is important in a wide array of procedures. The importance of such identification is particularly seen in that nucleated cells preparations often contain debris or other matter that can contribute to the overall noise, thereby decreasing the system's sensitivity.

Such cells are often identified by a nucleic acid dye which stains nucleic acids within the nucleus, permitting easy detection. However, when immunofluorescent markers are used, this approach suffers from the drawback that fluorescence signals from such nucleic acid dyes generally overlap and are much brighter than those of immunofluorescent dyes, and thus, tend to interfere with the observation of the immunofluorescent signal. While nucleic acid dyes which have emission spectra which do not overlap the emission spectra of immunofluorescent dyes are known, they are not practical for use in many instances To remedy this, researchers have tried to use lower (i.e., less than saturating) concentrations of the nucleic acid dyes, thereby reducing the magnitude of the signal (since this magnitude is a function of concentration). However, this procedure suffers from the drawback that the useful range of cell concentrations is greatly reduced as the fluorescence intensity in such circumstances is highly dependent on the number of cells in the sample. Further, when lower concentration of dye are used, the small amount of dye adsorbed onto the container surface also has a significant effect on the overall amount of dye available for staining nucleic acids, further affecting the sensitivity.

There exists a real need for a nucleic acid dye which can be used at or near saturating concentrations which will not interfere with the immunofluorescent signal.

SUMMARY OF INVENTION

This invention presents improved methodology for identification of nucleated cells in flow cytometric analysis when immunofluorescent dyes are also used. Briefly, the general method involves staining the nucleic acids with a fluorescent dye which can then be used to identify the nucleated cells by measurement of fluorescence on a flow cytometer.

The improvement presented by this invention is the use of a nucleic acid dye, or mixture of dyes, which gives low fluorescence at excitation conditions, so as not to greatly interfere with the signals of the immunofluorescent dyes, which dye or dye mixture can be used at a concentration sufficient to saturate the nucleic acid binding sites.

DETAILED DESCRIPTION OF THE INVENTION

Figure 1A:
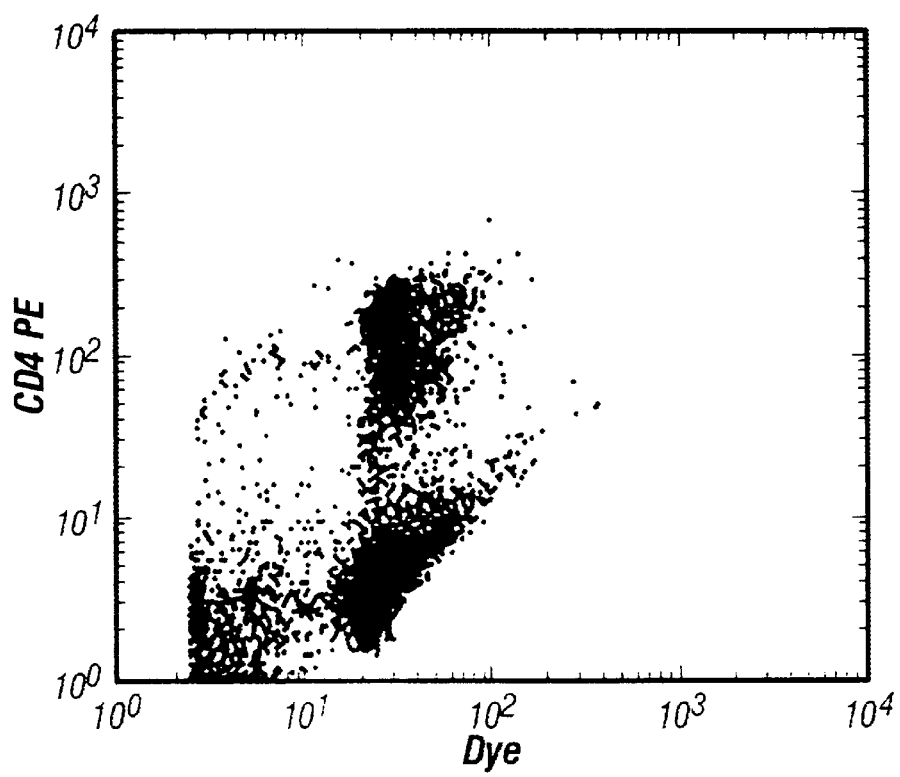
FIGS. 1A and 1B illustrates the staining results obtained with thioflavin T compared with the nucleic acid dye SY-VI-24. The dot plots show typical results for antibody staining (CD4-PE) versus nucleic acid dye using saturating concentration of thioflavin T (top panel) and very low, sub-saturating concentration of SY-VI-24 (bottom panel).

The instant invention presents a method for identifying nucleated cells in flow cytometric analyses. More specifically, the method comprises the steps of taking a body fluid sample from an individual, combining the fluid sample with a nucleic acid dye such as an RNA dye or a DNA dye, and one or more fluorescent antibodies each of which recognizes an antigen that is differentially expressed by different cells to form a labeled solution. The solution is then passed through a flow cytometer which measures fluorescence intensity and other fluorescent parameters and stores collected data for analysis. Each of the nucleic acid and immunofluorescent dyes must produce distinguishable emission spectra. As a practical matter, the emission spectra of the different dyes will have regions of spectra overlap.

In a preferred embodiment, the flow cytometer is equipped with a single laser for the excitation of the fluorescently labeled cells, such as an argon ion laser tuned to a wavelength of 488 nm.

The nucleic acid dye or dye mixture used must be one excitable at the same wavelength as the immunofluorescent dye, yet of sufficiently low fluorescent intensity so as not to interfere with the immunofluorescent dye signal(s). In a preferred embodiment, the dye is thioflavin T, which has the following structure:

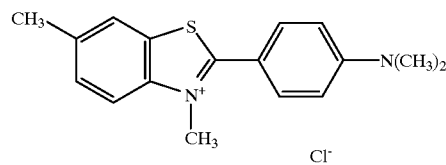

The dye is used at or near saturating concentration to permit simple identification of the nucleated cells.

Alternatively, a mixture of two or more nucleic acid dyes can be used. In such mixtures, one or more nucleic acid dyes which emit a fluorescent signal of moderate to high intensity when excited by the excitation source presented are admixed with one or more nucleic acid dyes which do not emit a fluorescent signal under these conditions. The ratio of the non-fluorescent dye(s) to fluorescent dye(s) is chosen such that effectively all nucleic acid binding sites are occupied, (i.e., at or near saturation) while only a low fraction of the dye bound will emit a fluorescent signal. Thus, this ratio will vary given the particular applications contemplated, and in particular, the strength of the fluorescent signal emitted by the immunofluorescence dye(s) used, as this will affect the magnitude of the nucleic acid dye signal which can be tolerated.

In a preferred embodiment, the mixture comprises the fluorescent dye, SY-VI-24 and non-fluorescent (at 488 nm excitation) dye chromycin A3 in a ratio of 1 ng/25 ug.

EXAMPLES

The following example illustrates a preferred embodiment of the instant invention but is not intended to be illustrative of all embodiments.

Example 1

Thioflavin T or another fluorescent nucleic acid dye, SY-VI-24, were used to stain whole blood or diluted whole blood by admixing 50 µL whole blood, 20 µL dye solution, and a phycoerythrin tagged anti-CD4 monoclonal antibody (CD4-PE). After staining the sample we diluted with approximately 0.5 ml of FACS® Lysing Solution.

Each sample was analyzed on a FACSort flow cytometer at an excitation wavelength of 488 mn and a 530/30 filter for green fluorescence and 585/42 filter for yellow fluorescence.

FIG. 3 illustrates dot plots of CD4-PE versus thioflavin T as a function of blood concentration using whole blood and blood diluted 1:10 and 1:100. Briefly, using subsaturating amounts of SY-VI-24 as the nucleic acid dye, a 10 fold decrease in blood cell concentration caused a 10 fold increase in fluorescence from the dye. When lymphocytes were stained simultaneously with SY-VI-24 and CD4 antibody conjugated to the yellow fluorescing tag phycoerythrin (PE), increased fluorescence from the SY-VI-24 decreased the ability to resolve the fluorescence due to CD4-PE. Using saturating amount of thioflavin T to stain whole blood, decreasing the blood cell concentration by 10 or 100 fold (by diluting the blood in buffer before staining) did not significantly change the intensity of thioflavin T fluorescence. In addition, the ability to resolve CD4-PE fluorescence was much improved by using thioflavin T rather than SY-VI-24 as the nucleic acid dye.

Figure 1B:
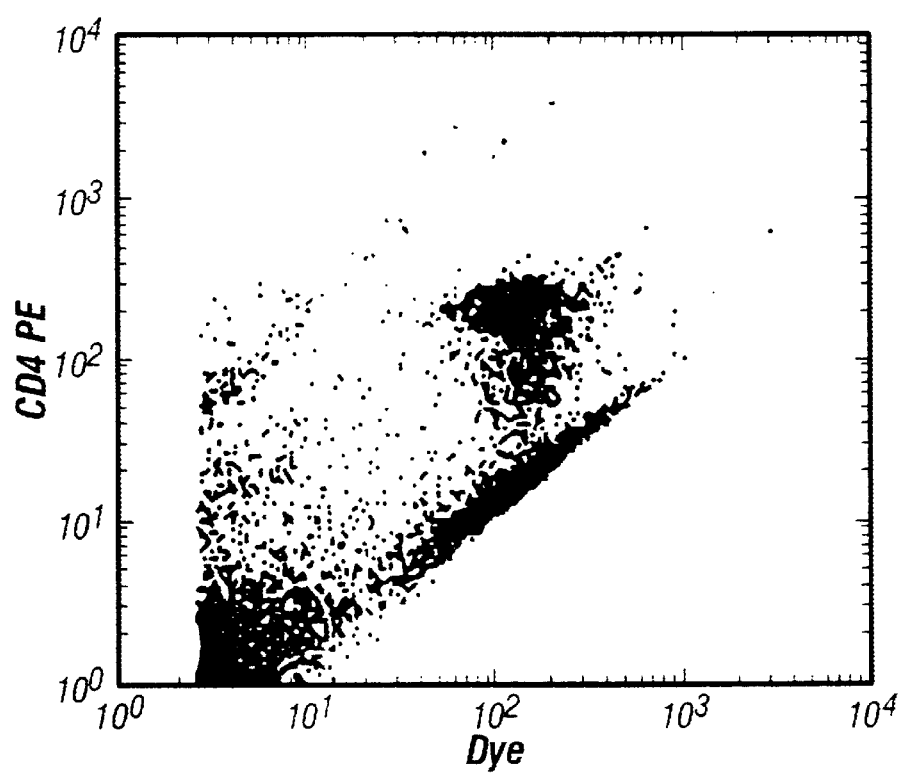

FIG. 1 illustrates the staining results obtained with thioflavin T compared with the nucleic acid dye SY-VI-24. The dot plots (show typical results for antibody staining (CD4-PE) versus nucleic acid dye using saturating concentration of thioflavin T (1a) dyes have primarily green fluorescence and PE has yellow fluorescence. SY-VI-24, like most green fluorescing dyes also emits a significant amount of yellow fluorescence which interferes with detecting the PE-labeled antibody. Thioflavin T emits much less yellow fluorescence even though it is used in much higher concentration than SY-IV-24. This is largely due to the fact that with 488 nm excitation, thioflavin T emits much less fluorescence at all wavelengths. The amount of green fluorescence from thioflavin T is adequate to identify nucleated cells, but not so bright that the yellow fluorescence from the dye interferes with detection of PE-labeled antibody. Separation of CD4-positive (CD4+ from CD4–) cells is much better when thioflavin T is used as the nucleic acid dye.

Example 2

The above experiment was repeated using a nucleic acid dye mixture, SY-VI-24 and chromycin A3 (CA3). Each test used 25 $\mu$g CA3 and 1 ng SY-VI-24, at saturating concentrations. The results are shown in FIG. 2.

Figure 2A:
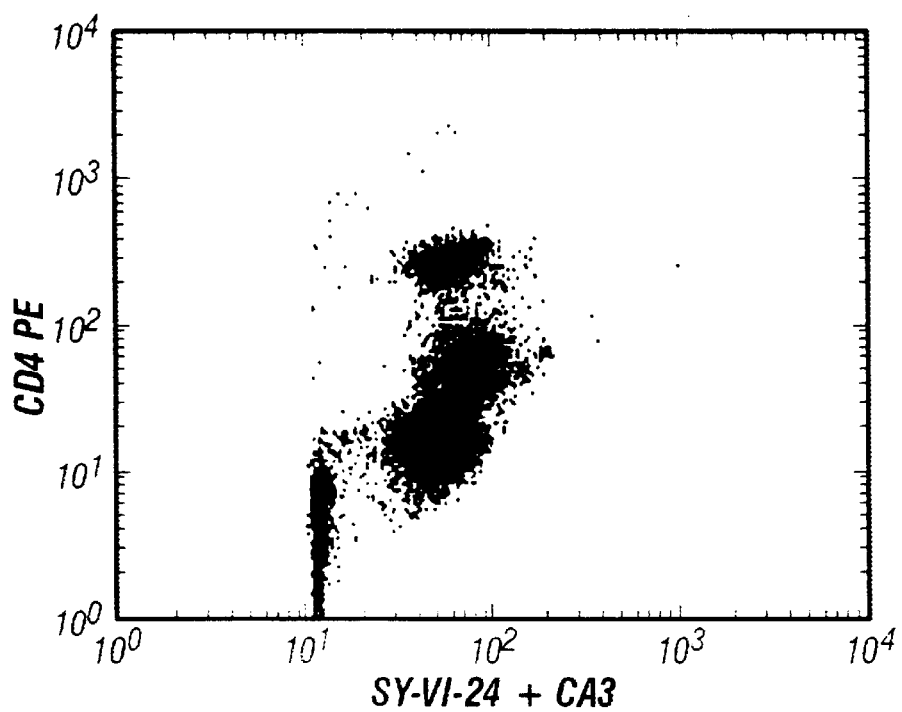
FIGS. 2A–2C shows dot plots of CD4-PE fluorescence versus nucleic acid stain fluorescence as a function of blood cell concentration, for the dye mixture SY-VI-24 and chromycin A3, using whole blood and blood diluted 1:8 and 1:32.
Figure 2B:
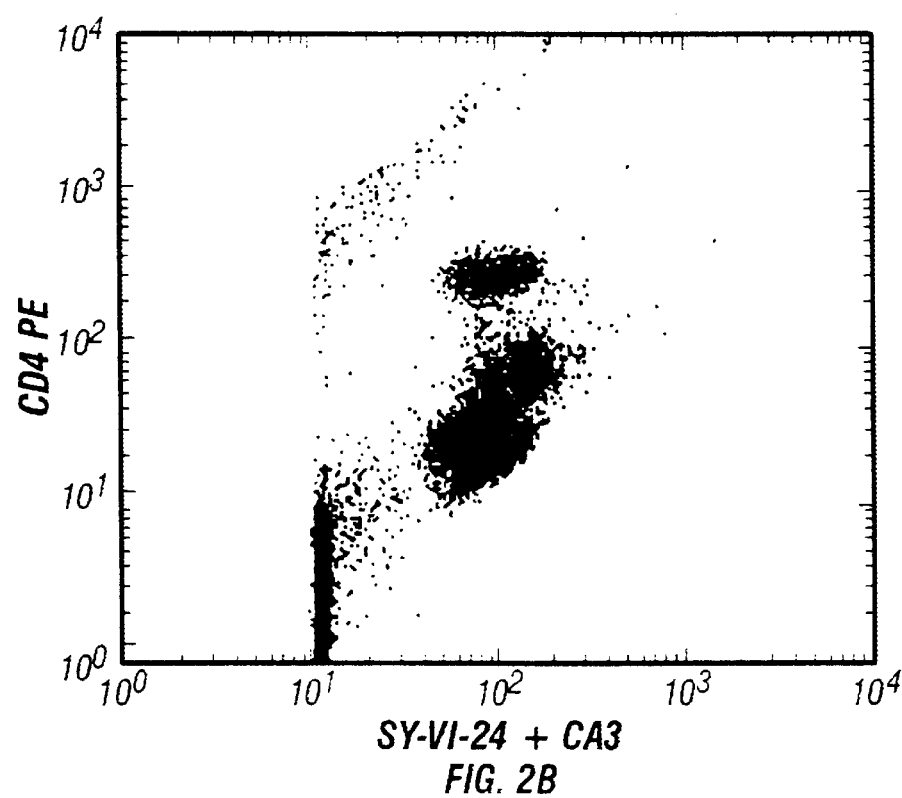
Figure 2C:
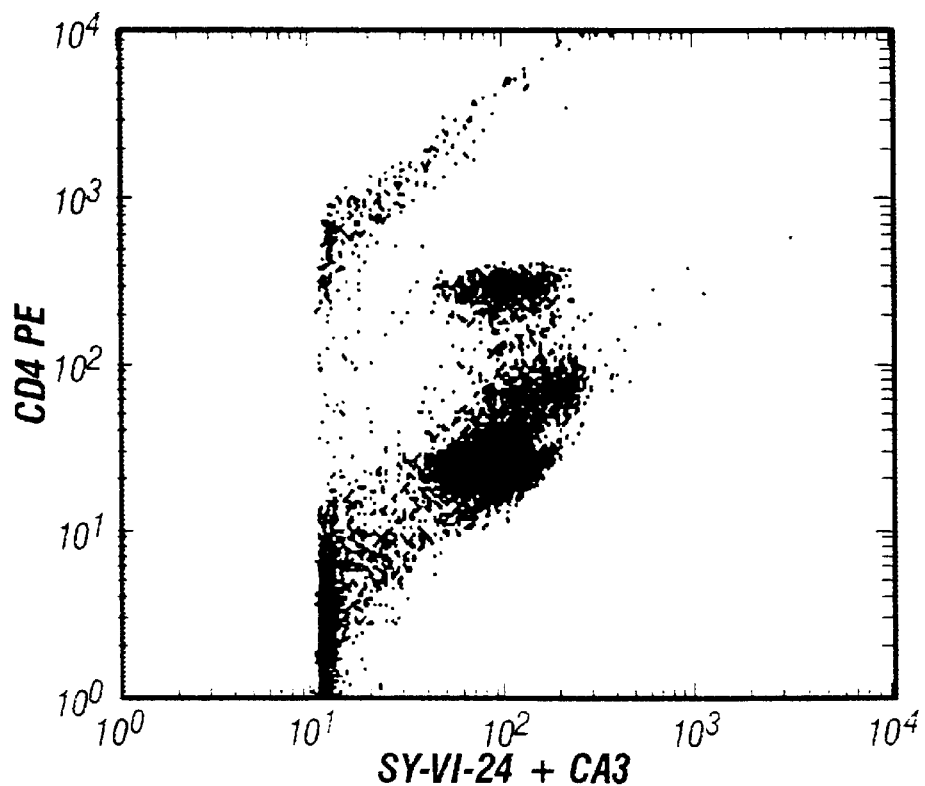

FIG. 2 shows dot plots of CD4-PE versus nucleic acid stain mixture as a function of blood cell concentration. Panels A–C in FIG. 2 show dot plots of CD4-PE versus nucleic acid dye fluorescence due to the mixture of SY-VI-24 and chromycin A3 (CA3). Results with whole blood are shown in FIG. 2A, and with blood diluted 1:8 and 1:32 before staining in FIGS. 2B and 2C, respectively. There is almost no difference in the results with blood cell concentration varied over this 32 fold range.

Figure 3A:
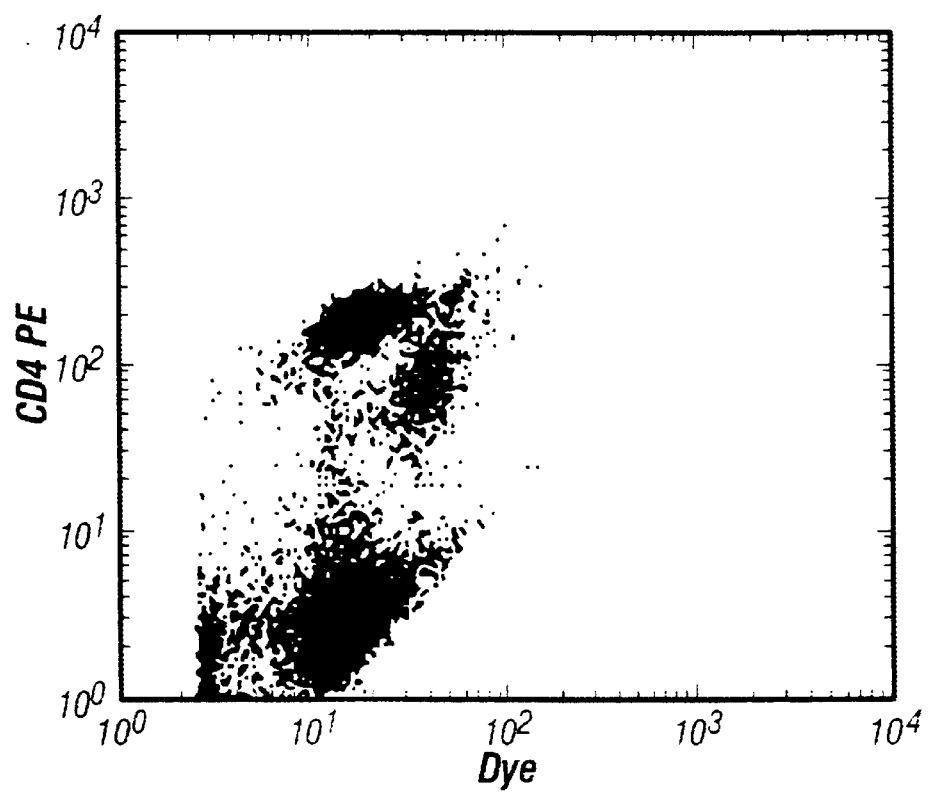
FIGS. 3A–3C shows dot plots of CD4-PE versus thioflavin T as a function of blood cell concentration using whole blood and blood diluted at 1:10 and 1:100.
Figure 3B:
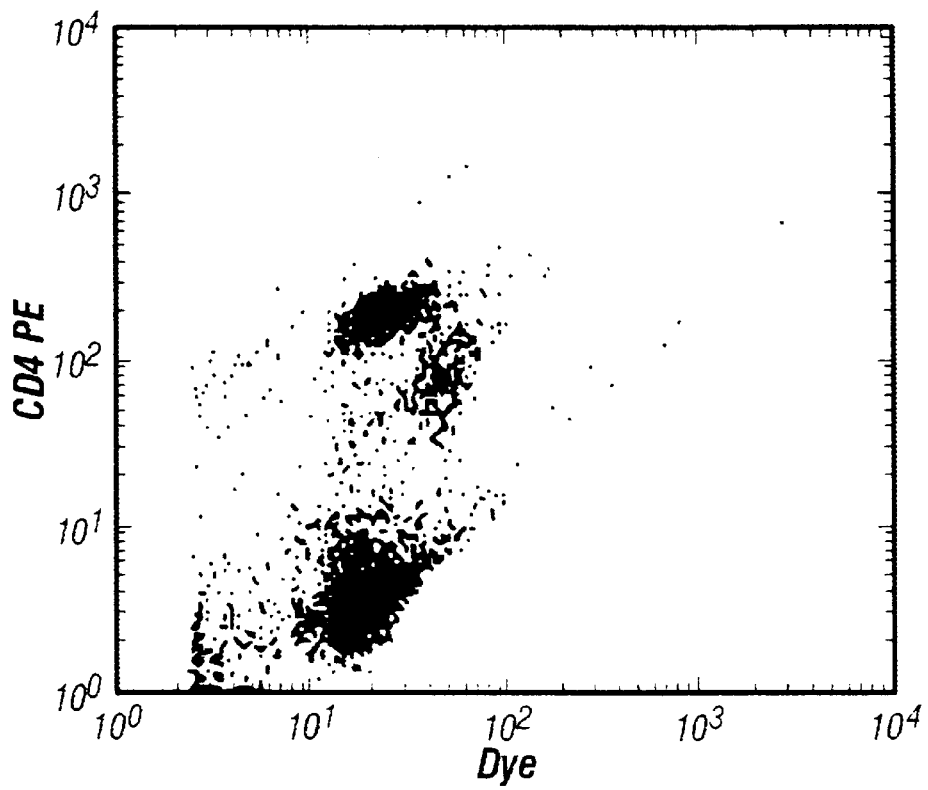
Figure 3C:
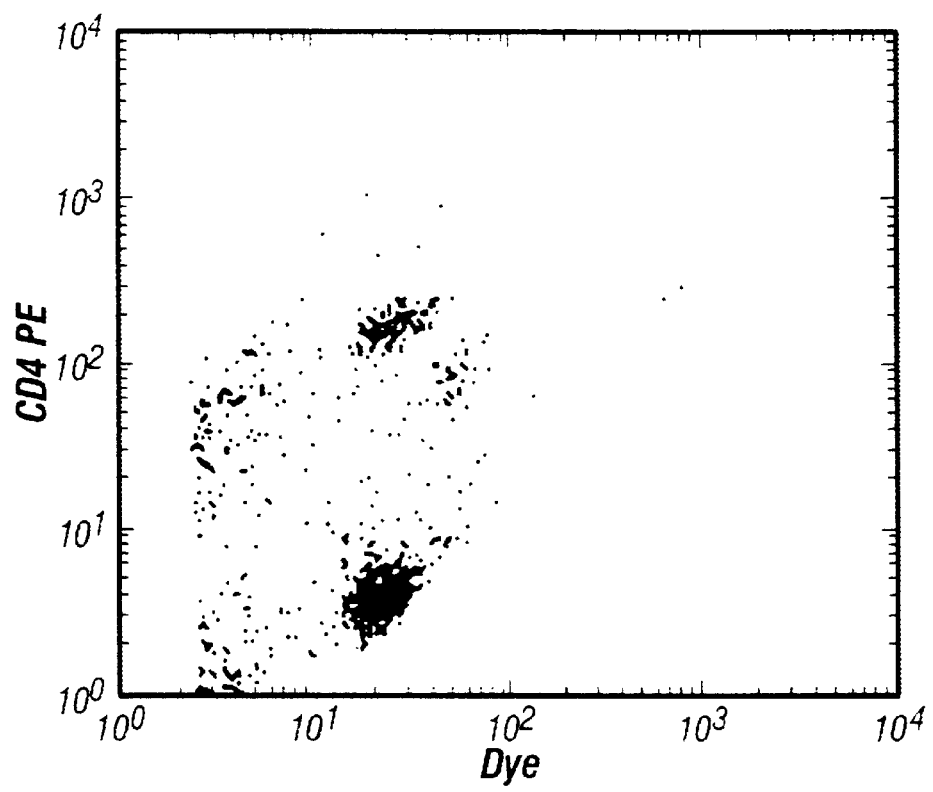

FIG. 3 shows similar results where a single dye, thioflavin T, is used at essentially saturating concentration to stain whole blood (FIG. 3A) or the same dye concentration is used to stain blood diluted 1:10 or 1:100 (FIGS. 3B and 3C respectively). Again, the results do not change significantly when the blood cell concentration is varied over a wide range.

It is apparent that many modifications and variations this invention as hereinabove set forth may be made without departing from the spirit and scope thereof the specific embodiments are given by way of example only and the invention is limited only by the terms of the appended claims.

What is claimed is:

1. A multi-parameter, flow cytometric method of identifying nucleated cells in a blood sample, the method comprising:
    (a) contacting a blood sample with (i) a saturating concentration of a fluorescent nucleic acid dye, and (ii) a fluorophore-labeled antibody, said antibody capable of binding to at least a subset of nucleated cells in said sample;
    (b) exciting said dye at a wavelength sufficiently offset from said dye's excitation maximum that said dye's fluorescence emission does not interfere with quantitative detection of excited emission from said fluorophore; and
    (c) flow cytometrically measuring dye and fluorophore fluorescence emissions,
        said measured fluorescence emissions identifying nucleated cells in said sample.

2. The method of claim 1 wherein said fluorophore labeled antibody is a monoclonal antibody.

3. The method of claim 1 wherein said fluorophore is phycoerythrin (PE).

4. The method of claim 1 wherein said fluorophore labeled antibody is an anti-CD4 antibody.

5. The method of claim 3 wherein said PE labeled antibody is an anti-CD4 antibody.

6. The method of claim 5 wherein said PE labeled anti-CD4 antibody(CD4-PE) is monoclonal.

7. The method of claim 1 wherein said fluorophore labeled antibody and said dye are commonly excited by a single laser.

8. The method of claim 7 wherein said single laser emits at a wavelength of about 488 nm.

9. The method of claim 1 wherein said dye has an excitation maximum at a lower wavelength than that used for excitation.

10. The method of claim 1 wherein said dye is thioflavin T.

11. The method of claim 1 wherein the sample is whole blood.

12. The method of claim 1 wherein said nucleated cells are white blood cells.

13. In a method of identifying nucleated cells in a blood sample using a nucleic acid dye and a fluorophore-labeled antibody in multiparameter flow cytometric analysis, the improvement comprising:
    using saturating concentrations of a nucleic acid dye having an excitation maximum sufficiently offset from the wavelength used for fluorescence excitation in said analysis that fluorescence emission from said dye can be detected concurrently with, and without interfering with, quantitative detection of fluorescence emission from said fluorophore.

* * * * *